United States Patent
Ikejima et al.

(10) Patent No.: US 12,385,900 B2
(45) Date of Patent: Aug. 12, 2025

(54) METHOD FOR EVALUATING CYTOTOXICITY OF GAS

(71) Applicants: DAIKIN INDUSTRIES, LTD., Osaka (JP); THE UNIVERSITY OF TOKYO, Tokyo (JP)

(72) Inventors: Ikumi Ikejima, Osaka (JP); Hiroshi Matsumoto, Osaka (JP); Kohei Sawada, Tokyo (JP)

(73) Assignees: DAIKIN INDUSTRIES, LTD., Osaka (JP); THE UNIVERSITY OF TOKYO, Tokyo (JP)

( * ) Notice: Subject to any disclaimer, the term of this patent is extended or adjusted under 35 U.S.C. 154(b) by 1117 days.

(21) Appl. No.: 17/255,798

(22) PCT Filed: Jun. 26, 2019

(86) PCT No.: PCT/JP2019/025400
§ 371 (c)(1),
(2) Date: Dec. 23, 2020

(87) PCT Pub. No.: WO2020/004470
PCT Pub. Date: Jan. 2, 2020

(65) Prior Publication Data
US 2021/0148887 A1    May 20, 2021

(30) Foreign Application Priority Data
Jun. 28, 2018  (JP) .................. 2018-122876

(51) Int. Cl.
*A61K 49/00* (2006.01)
*G01N 33/487* (2006.01)
*G01N 33/497* (2006.01)

(52) U.S. Cl.
CPC ..... *G01N 33/48742* (2013.01); *G01N 33/497* (2013.01)

(58) Field of Classification Search
CPC ........... A61K 49/223; G01N 33/48742; G01N 33/497
USPC ...................................... 424/9.52
See application file for complete search history.

(56) References Cited

U.S. PATENT DOCUMENTS

| | | |
|---|---|---|
| 2015/0082864 A1 | 3/2015 | Chen et al. |
| 2020/0333317 A1 | 10/2020 | Virtanen |
| 2021/0215653 A1 | 7/2021 | Aponte Torrealba et al. |
| 2021/0285926 A1 | 9/2021 | Ikejima et al. |

FOREIGN PATENT DOCUMENTS

| | | |
|---|---|---|
| CN | 101580869 A | 11/2009 |
| CN | 106124647 A | 11/2016 |
| CN | 107121553 A | 9/2017 |
| JP | 2003-510093 A | 3/2003 |
| JP | 2005-523022 A | 8/2005 |
| JP | 2013-039099 A | 2/2013 |
| WO | 01/23886 A1 | 4/2001 |
| WO | 03/089635 A1 | 10/2003 |

OTHER PUBLICATIONS

Masumi et al. Mut res 2008, 652, pp. 122-130.*
Akiko Furuyama, "Gas-liquid interface cell exposure device that directly exposes air pollutants to cells", National Institute for Environmental Studies, Oct. 31, 2013, Retrieved from : URL: <https://www.nies.go.jp/kanko/news/32/32-4/32-4-03.html>(10 pages total).
Shiraishi et al., "Study on the Screening Test of Genotoxicity to Volatile and Insoluble Compounds such as Halon Replacements Using Mammalian Cell Culture", Journal of Environmental Chemistry, 1996, vol. 6, No. 2, pp. 217-224.
International Search Report of related PCT/JP2019/029140 dated Oct. 15, 2019 [PCT/ISA/210].
Wolfram E. Samlowski et al., "Nitric Oxide Exposure Inhibits Induction of Lymphokine-Activated Killer Cells by Inducing Precursor Apoptosis", Nitric Oxide: Biology and Chemistry, 1998, pp. 45-56, vol. 2, No. 1, Article No. NO980169.
Kikuo Komori et al., "Simplified Toxicity Evaluation for Gaseous Sample Based on In vitro Bioassay", Monthly Journal of the Institute of Industrial Science, pp. 89-92, 2007, vol. 59, No. 2.
International Search Report of PCT/JP2019/025400 dated Sep. 10, 2019 [PCT/ISA/210].
Bothun et al., "Molecular and Phase Toxicity of Compressed and Supercritical Fluids in Biphasic Continuous Cultures of *Clostridium thermocellum* ", Biotechnology and Bioengineering, vol. 89, No. 1, Nov. 11, 2004, pp. 32-41 (10 pages total).
Extended European Search Report dated Feb. 15, 2022 from the European Patent Office in EP Application No. 19826191.9.
Extended European Search Report dated Mar. 23, 2022 from the European Patent Office in EP Application No. 19841930.1.
Notice of Allowance issued Feb. 15, 2024, in U.S. Appl. No. 17/261,212.

* cited by examiner

*Primary Examiner* — Robert B Mondesi
*Assistant Examiner* — Mohammad Y Meah
(74) *Attorney, Agent, or Firm* — Sughrue Mion, PLLC

(57) ABSTRACT

A method for evaluating the cytotoxicity of a gas, the method being applicable to cells present in a cell culture medium, namely, to cells other than bronchial- or lung-derived cells. The method including: a gas dissolution step for dissolving a gas in a cell culture medium, and a cell evaluation step for measuring a cell function, in this order.

7 Claims, 1 Drawing Sheet

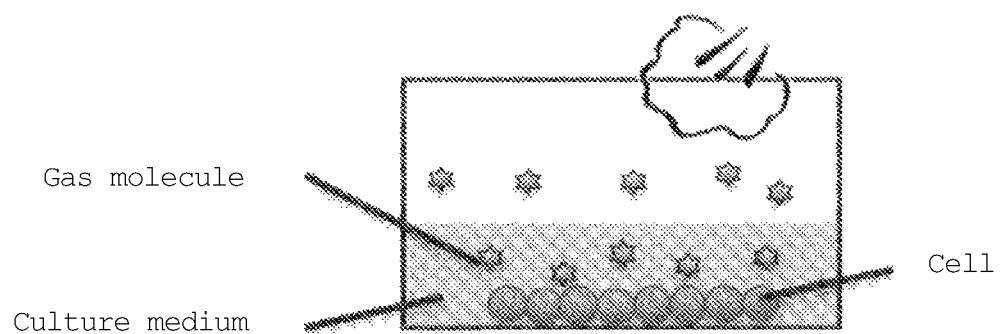

METHOD FOR EVALUATING CYTOTOXICITY OF GAS

CROSS REFERENCE TO RELATED APPLICATIONS

This application is a National Stage of International Application No. PCT/JP2019/025400, filed Jun. 26, 2019, claiming priority to Japanese Patent Application No. 2018-122876, filed Jun. 28, 2018.

TECHNICAL FIELD

The present disclosure relates to a method for evaluating the cytotoxicity of a gas.

BACKGROUND ART

Patent Literature (PTL) 1 suggests evaluating the toxicity of a test substance by performing cell culture with a test substance contained in a cell culture medium, and measuring the state of the cells.

The evaluation method described in PTL 1 is utilized for the selection of a candidate compound (solid or liquid) in the research and development of medicines.

Non-patent literature (NPL) 1 suggests a method for evaluating the toxicity of a gas at the in vitro level. A semi-permeable membrane is provided at the air-liquid interface between the gas and the cell culture medium, and cells are cultured on the semi-permeable membrane. Then, the cells cultured on the semi-permeable membrane are directly exposed to a gas as a test substance, and the cytotoxicity of the gas is evaluated. This method allows the evaluation of gas toxicity to A549 cells or Calu-3 cells.

CITATION LIST

Patent Literature

PTL 1: JP2003-510093A

Non-patent Literature

NPL 1: Monthly Journal of the Institute of Industrial Science, Vol. 59, No. 2, 2007, pp. 89-92

SUMMARY OF INVENTION

Technical Problem

Solution to Problem

An object of the present disclosure is to provide a method for evaluating the cytotoxicity of a gas, the method being applicable to cells present in a cell culture medium; i.e., to cells other than bronchial- or lung-derived cells.

Means for Solving the Problem

As a result of extensive research to achieve the above object, the inventors found that by dissolving a gas as a test substance in a cell culture medium, the toxicity of the gas to cells can be evaluated. Based on this finding, the inventors conducted further research, and accomplished the present disclosure.

Specifically, the present disclosure provides the following toxicity evaluation methods.

Item 1. A method for evaluating the toxicity of a gas to cells, comprising:
a gas dissolution step for dissolving a gas in a cell culture medium, and
a cell evaluation step for measuring a cell function, in this order.

Item 2. The method according to Item 1, wherein the gas dissolution step is performed by maintaining the cell culture medium at a pH of 7.1 to 7.7, and a temperature of 35 to 39° C.

Item 3. The method according to Item 1 or 2, wherein the gas dissolution step is performed by bringing the gas into contact with the surface of the cell culture medium to dissolve the gas in the culture medium.

Item 4. The method according to any one of Items 1 to 3, wherein the cells are derived from mammals.

Advantageous Effects of Invention

According to the toxicity evaluation method of this disclosure, the toxicity of a gas to cells present in a cell culture medium can be evaluated. Therefore, this method can be applied to cells other than bronchial- or lung-derived cells, which have thus far been unable to be evaluated.

BRIEF DESCRIPTION OF DRAWINGS

The Figure is a schematic diagram of the method for evaluating toxicity to cells according to this disclosure.

DESCRIPTION OF EMBODIMENTS

The method for evaluating the toxicity of a gas to cells includes a gas dissolution step for dissolving a gas in a cell culture medium, and a cell evaluation step for measuring a cell function, in this order.

The gas as a test subject is not limited, as long as it is a gas. However, considering the purpose, i.e., toxicity evaluation, the gas is preferably a gas that is subjected to toxicity evaluation. The gas as a test subject may be a single gas, or a mixture of several gases.

Examples of such gases include air pollutants, such as nitrogen oxides and sulfur oxides; exhaust gases, such as carbon monoxide, carbon dioxide, and hydrocarbons; fuel gases, such as methane, propane, butane, and acetylene; gases emitted from products, such as formaldehyde, toluene, xylene, paradichlorobenzene, ethylbenzene, and styrene; hydrofluorocarbons (HFCs), hydrochlorofluorocarbons (HCFCs), hydrofluoroolefins (HFOs), and hydrochlorofluoroolefins (HCFOs); and gases emitted during production processes, such as monomer gases.

Of these, from the viewpoint of high industrial value, fuel gases, such as methane, propane, butane, and acetylene; gases emitted from products, such as formaldehyde, toluene, xylene, paradichlorobenzene, ethylbenzene, and styrene; gases for refrigerants, such as HFCs, HCFCs, HFOs, and HCFOs; and gases emitted during production processes, such as monomer gases, can be preferably evaluated.

Any cultured cells can be used as cells for toxicity evaluation. Examples include primary cultured cells, and passage cultured cells. The cultured cells may be attached to the bottom of a cell culture vessel, or may float in a cell culture medium. Naturally, the cells can be semi-floating cells.

Regarding the cells to be used for toxicity evaluation, a single kind of cells may be used, or several kinds of cells may be used.

Although any kind of cultured cell can be used for toxicity evaluation, as described above, mammalian-derived cells are preferable in light of the purpose, i.e., toxicity evaluation.

Depending on the purpose of toxicity evaluation, cells derived from suitable parts of the body can be used. Examples include at least one member selected from cardiomyocytes, liver cells, kidney cells, brain cells, nerve cells, lung cells, gastrointestinal cells, pancreatic cells, spleen cells, endometrial cells, fibroblasts, skin cells, myocytes, blood cells, and bone marrow cells.

The type of medium used as the cell culture medium may be suitably determined according to cells used. Specifically, an MEM medium, a DMEM medium, a BME medium, a Ham's F-12 medium, or an RPMI 1640 medium can be used.

The number and density of cells to be seeded and the size of the cell culture vessel may be suitably determined according to the purpose of the toxicity evaluation and the type of cells.

The toxicity evaluation method of this disclosure includes a gas dissolution step for dissolving a gas in a cell culture medium.

When the gas is dissolved in the cell culture medium, the pH of the cell culture medium is preferably maintained at 7.1 to 7.7 using carbon dioxide, buffer, or the like; and more preferably 7.3 to 7.5, to eliminate the possibility that the condition of the cells is affected by a factor other than the gas. For the same reason, the temperature of the cell culture medium is preferably maintained at 35 to 39° C., and more preferably 36 to 38° C.

As the method for dissolving a gas in a cell culture medium, a suitable method can be employed; the method is not limited. Examples include a method for bubbling a gas in a cell culture medium, and a method for allowing a gas to flow on the surface of a cell culture medium (in other words, the gas is brought into contact with the surface of the cell culture medium to dissolve the gas in the culture medium). In this case, the concentration of the gas to be introduced into the surface of the cell culture medium can be set to any concentration greater than 0 vol % and less than 100 vol %. The concentration of carbon dioxide required for cell culture is not limited, and can be set to any concentration greater than 0 vol % and less than 10 vol %.

Of these, since the pH and temperature of the cell culture medium can be suitably maintained in the numerical ranges described above, the method for flowing a gas on the surface of the cell culture medium is preferable.

As a specific embodiment for flowing a gas on the surface of a cell culture medium, there is an embodiment in which an open cell culture vessel is provided to a container (incubator) having at least one gas inlet and at least one gas outlet to flow the gas therein.

The air pressure in the container (incubator) when the gas flows in the container (incubator) is preferably maintained at 90 to 120 kPa.

The size of the container having at least one gas inlet and at least one gas outlet may be suitably determined according to the size of the cell culture vessel. The flow rate for flowing the gas may also be suitably determined according to the size of the container having at least one gas inlet and at least one gas outlet, and the size of the cell culture vessel.

Further, in order to specifically, clearly, and accurately understand the cytotoxicity of a gas, the cytotoxicity evaluation method of this disclosure also includes a cell evaluation step for evaluating cell function after the gas dissolution step.

Examples of cell functions to be evaluated include cell viability, mitochondrial functions, cell replication capacity, intracellular energy balance, and cell membrane integrity. It is also preferable to evaluate functions specific to cells according to the cell type. For example, in the evaluation of cardiomyocytes, evaluating the beat index thereof is also preferable.

In this specification, cell viability is defined as the ratio of the number of live cells to the total number of live and dead cells. The number of live cells and the number of dead cells can be obtained in a dye exclusion test using a vital staining agent.

In this specification, mitochondrial functions are defined as functions indicated by changes in oxygen consumption rate, calcium ion flow rate, and membrane potential in mitochondria. The change in oxygen consumption rate in mitochondria can be obtained by measuring the emission intensity of an oxygen-sensitive probe. The change in calcium ion flow rate can be obtained by measuring the emission intensity of a calcium ion-sensitive probe. The change in membrane potential can be obtained by measuring the luminescence intensity of a membrane potential-sensitive probe.

In this specification, intracellular energy balance is defined as the ADP/ATP volume ratio. The ADP/ATP volume ratio can be obtained by measuring the chemiluminescence intensity by a luciferase reaction.

In this specification, cell membrane integrity is defined as the degree of cell membrane damage. The degree of cell damage can be obtained by the measurement of deviant enzymes such as LDH.

The embodiments of this disclosure are described above; however, this disclosure is not limited to these examples. The present disclosure can be performed with various embodiments, as long as these embodiments do not deviate from the gist of this disclosure.

EXAMPLES

Embodiments of this disclosure will be described in more detail with reference to the Examples below; however, the present disclosure is not limited to these Examples.
Cytotoxicity Evaluation Test Human iPS cell-derived cardiomyocytes (iCell cardiomyocytes[2], CDI) were seeded into a 96-well half-area plate at a density of 40,000 cells/well, followed by culture in an incubator for 7 to 10 days. Subsequently, a Ca indicator (EarlyTox Cardiotoxicity Kit, Molecular Devices) was added at 30 µL/well to the cardiomyocytes. Subsequently, chlorodifluoromethane (Example) or difluoromethane (Reference Example) was allowed to flow onto the surface of the cell culture medium in a closed vessel at a flow rate of 50 mL/min. During the flow, the cell culture medium was maintained at a pH of 7.4, a temperature of 37° C., and an air pressure in the incubator of 101.3 kPa. The number of beats of cardiomyocytes from the start of the flow to 10 minutes after the start of the flow was measured by a fluorescence measurement with a confocal quantitative image cytometer (CQ1, Yokogawa Electric Corporation).

Experiments on animals have reported that chlorodifluoromethane is a gas that has effects on the heart. In contrast, difluoromethane is known to have no significant effects on the heart; thus, it was used as a negative control (Reference Example).

As shown in Table 1, in the reference example using difluoromethane (negative control), almost no change in the number of beats of cardiomyocytes was observed when the difluoromethane was dissolved in the cell culture medium. It was confirmed that flowing a gas that is harmless to cardiomyocytes onto the surface of the cell culture medium alone had no effect on cardiomyocytes, and that the cardiomyocytes were maintained in a healthy state.

In contrast, in the example using chlorodifluoromethane, which is known to have effects on the heart, a significant increase in the number of beats was observed 10 minutes after the start of the flow (a 74% increase). In view of the above, it was confirmed that the toxicity evaluation method of this disclosure can evaluate the toxicity of the gas (chlorodifluoromethane) to cardiomyocytes.

TABLE 1

| Exposure time/min. | Example Average number of beats (beats/30 sec) | Reference Example Average number of beats (beats/30 sec) |
|---|---|---|
| 0 | 14.5 | 16.1 |
| 10 | 25.3 | 16.5 |

The invention claimed is:

1. A method for evaluating a toxicity of a gas to cells, comprising:
   a gas dissolution step for dissolving a gas in a cell culture medium containing cells, wherein the cell culture medium containing the cells is in an open cell culture vessel and the open cell culture vessel is in a container having at least one gas inlet and at least one gas outlet,
   wherein the gas dissolution step comprises allowing the gas to flow through the at least one gas inlet and the at least one gas outlet, whereby the gas is brought into contact with a surface of the cell culture medium,
   wherein the gas dissolution step is performed while maintaining the cell culture medium at a pH of 7.1 to 7.7, and a temperature of 35 to 39° C.; and
   a cell evaluation step for measuring a cell function, in this order,
   wherein the cells are cardiomyocytes and the cell function is a number of beats of a cardiomyocyte per time interval, and
   wherein the gas is chlorodifluoromethane.

2. The method according to claim 1, wherein the cells are mammalian cells.

3. The method according to claim 1, wherein a flow rate of the gas through the at least one inlet and the at least one outlet is 50 mL/min.

4. The method according to claim 1, wherein an air pressure in the container having the at least one gas inlet and the at least one gas outlet is 101.3 kPa.

5. A method for evaluating a toxicity of a gas to cells, comprising:
   a gas dissolution step for dissolving a gas in a cell culture medium containing cells by bubbling the gas through the cell culture medium, and
   a cell evaluation step for measuring a cell function, in this order,
   wherein the cell function is one or more selected from the group consisting of cell viability, mitochondria, mitochondrial functions, cell replication capacity, intracellular energy balance, cell membrane integrity, and a function specific to a type of the cells contained in the cell culture medium.

6. The method according to claim 5, wherein the cells are cardiomyocytes and the cell function is a number of beats of a cardiomyocyte per time interval.

7. The method according to claim 6, wherein the gas is chlorodifluoromethane.

* * * * *